(12) United States Patent
Abbasi et al.

(10) Patent No.: US 6,912,905 B2
(45) Date of Patent: Jul. 5, 2005

(54) AUTOMATED TOOL FOR ULTRASONIC INSPECTION OF BRAZED JOINTS

(75) Inventors: Waheed A. Abbasi, Murrysville, PA (US); Scott A. Karstetter, Monroeville, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 0 days.

(21) Appl. No.: 10/617,531

(22) Filed: Jul. 11, 2003

(65) Prior Publication Data

US 2005/0005700 A1 Jan. 13, 2005

(51) Int. Cl.[7] .............................................. G01N 29/10
(52) U.S. Cl. ........................................ 73/588; 73/620
(58) Field of Search .......................... 73/588, 620, 622, 73/633

(56) References Cited

U.S. PATENT DOCUMENTS

| | | | |
|---|---|---|---|
| 3,777,552 A | * | 12/1973 | Fletcher et al. ............... 73/622 |
| 3,921,440 A | * | 11/1975 | Toth ............................ 73/622 |
| 4,170,144 A | | 10/1979 | Scott |
| 4,201,093 A | | 5/1980 | Logan |
| 4,290,310 A | | 9/1981 | Anderson |
| 4,385,521 A | | 5/1983 | Hagen et al. |
| 4,429,576 A | | 2/1984 | Norris |
| 4,457,176 A | | 7/1984 | Scholz |
| 4,531,413 A | | 7/1985 | Tsuchita et al. |
| 4,700,572 A | | 10/1987 | Senba et al. |
| 5,065,763 A | | 11/1991 | Green et al. |
| 5,339,691 A | | 8/1994 | Smith et al. |
| 5,696,326 A | * | 12/1997 | Becherucci et al. .......... 73/588 |
| 6,365,873 B1 | | 4/2002 | Smartt et al. |
| 6,497,150 B1 | | 12/2002 | Kruzic |

* cited by examiner

Primary Examiner—John E. Chapman

(57) ABSTRACT

An ultrasonic inspection tool (100) for inspecting the brazed joint (76) between two generator stator coils (18A and 18B) and an interconnecting copper bar (74). The inspection tool (100) is automatically serially positioned at a plurality of inspection sites on the surface of the copper bar (74). At each site an ultrasonic signal is emitted from the tool (100) and the return echo is sensed. Analysis of the return echo at each of the plurality of sites determines the characteristics of the brazed joint (76) at the site, from which a determination can be made as to the quality of the joint between coils (18A and 18B) and the copper bar (74).

10 Claims, 7 Drawing Sheets

AUTOMATED TOOL FOR ULTRASONIC INSPECTION OF BRAZED JOINTS

FIELD OF THE INVENTION

The present invention relates generally to electric generators, and more particularly to a method and apparatus for inspecting joints within the generator stator windings.

BACKGROUND OF THE INVENTION

An electric generator produces electricity according to the principles of generator action of a dynamoelectric machine, in response to a turning torque provided by a combustion or steam-driven turbine. The generator is a mechanically massive structure and electrically complex, with typical output power ratings up to 1,500 MVA at voltages up to 26 kilovolts (kV).

Conventionally, the electric generator comprises a rotor carrying axial field windings (also referred to as rotor windings) for producing a magnetic flux field in response to an input current, which is typically direct current supplied from a separate exciter. One end of the rotor shaft is drivingly coupled to a steam or gas-driven turbine for providing rotational energy to turn the rotor. Rotation of the rotor within stationary stator windings (also referred to as armature windings) causes the rotor magnetic field to induce an output current in the stator windings.

As shown in FIG. 1, conventionally an electric generator 10 comprises a rotor 12 carrying axial field or rotor windings 13 for producing a magnetic flux field that rotates within a stationary stator 14. One end 15 of the rotor 12 is drivingly coupled to a steam or gas driven turbine (not shown in FIG. 1) for providing rotational torque to turn the rotor 12. An opposing end 16 is coupled to a separate exciter (not shown) for providing direct current supplied to the rotor windings 13.

The stator 14 comprises a core 17 including a plurality of thin, high-permeability circumferential slotted laminations placed in a side-by-side orientation and insulated from each other to reduce eddy current losses. Stator coils 18 are disposed within inwardly directed slots of the stator core 17, and interconnected to form one or more closed-circuit stator windings. Rotation of the axial field windings causes the magnetic field produced thereby to induce alternating current in the stator coils 18. The generated current is carried to the main leads 19 for connection to an external electrical load. Three-phase alternating current is supplied from a generator having three independent stator phase windings, formed by appropriate interconnection of a plurality of stator coils 18, and spaced at 120° around the stator core. Single-phase alternating current is supplied from a single stator coil extending 360° around the stator core.

The rotor 12 and the stator 14 are enclosed within a frame 20. Each rotor end comprises a bearing journal (not shown) for mating with bearings 30 attached to the frame 20. The rotor 12 further carries a blower 32 for forcing cooling fluid through the generator elements. The cooling fluid is retained within the generator 10 by seals 34 located where the rotor ends penetrate the frame 20. The cooling fluid is supplied to coolers 36 for releasing the heat absorbed from the generator components, after which the coolant is recirculated back through the generator elements.

FIG. 2 is a cross-sectional view of the stator 14, illustrating a face 60 of one stator core lamination and inwardly directed slots 62 carrying a top coil 18A and a bottom coil 18B. The individual core laminations are coupled by clamp structures 64 to form the stator core 17.

FIGS. 3A and 3B illustrate one end of the top coil 18A and the bottom coil 18B, each comprising two groups or columns of conductive strands 66 and a plurality of cooling ducts 67 disposed between each strand group. The cooling ducts 67 remove heat energy produced by current flow through the top and bottom coils 18A and 18B. As shown, the top and bottom coils 18A and 18B are separated by a void 68. Consolidation clips 70, typically constructed from copper, encircle and capture a conductive strand group at the end region of the conductive strands 66. Thus four consolidation clips 70 are shown in FIG. 3A. A similar arrangement of conductive strands, cooling ducts and consolidation clips is present at the opposing end of the top coil 18A and the bottom coil 18B.

It is known by those skilled in the art that other generator configurations comprise a stator coil including only a single coil such as the top coil 18A or the bottom coil 18B. In such a configuration only two consolidation clips are required, one consolidation clip for each strand group, with the two groups separated by cooling ducts. In still another configuration, a stator coil comprises only a single group of conductive strands, absent cooling ducts, with the strand group retained by one consolidation clip.

To form closed-circuit phase windings of the stator 14, the conductive strands 66 of the top coil 18A are electrically connected to the conductive strands 66 of the bottom coil 18B. Connected top and bottom coils 18A and 18B are then further connected to other interconnected top and bottom coils to form the closed-circuit stator phase windings. One known technique for effecting this connection between the top coil 18A and the bottom coil 18B brazes or solders an interconnecting copper bar 74 to opposing sides of both the top and bottom coils 18A and 18B. See FIGS. 4 and 5. An overlap region between the consolidation clip 70 and the copper bar 74 is indicated generally by reference character 76 in FIG. 4. Note from FIG. 5 that there are four such overlap regions, one on each opposing side of both the top coil 18A and the bottom coil 18B.

In certain coil embodiments, the overlap width is about one inch to about 1.25 inches, and the overlap length (designated "L" in FIG. 4) is dependent upon the coil height, (i.e., the distance between top coil 18A and the bottom coil 18B), which is typically in the range of about 3 inches to 5 inches. Assuming a coil height of 4 inches, each overlap region 76 presents an area of about 4 square inches. In certain other stator embodiments, the consolidation clip is replaced by a copper block that encircles the coil strands. Generally, the overlap region is larger in the embodiment employing the copper block.

After the brazing operation, the overlap region must be inspected to ensure that a high quality braze joint has been formed between the copper bar 74 and the consolidation clips 70. Inspection of the copper bar braze joints at the end of each stator coil is a critical element of generator installation. The inspection is advisable to determine the integrity of the braze joint and ensure that the performance of the generator will not be compromised by a braze joint failure. In addition to conducting an inspection during construction of the generator, the brazed joint is also inspected when a stator coil is rewound. An overlap inspection is also performed in those generator embodiments employing a copper block in lieu of a consolidation clip.

One prior art inspection process utilizes a stencil template in the form of a grid with quarter-inch grid squares for identifying individual inspection sites. An inspector places the stencil over the copper bar 74 in the overlap region 76, and using the grid squares as a guide, manually marks each inspection site to guide the subsequent inspection process. The stencil is removed and a couplant material (typically a gel-like substance) is applied to the copper bar 74 in the overlap region 70. An ultrasonic transducer is then manually positioned over each inspection site, as marked on the copper bar 74, for inspecting the quality of the braze joint at that site. The ultrasonic transducer emits ultrasonic energy (in one embodiment at about 2.25 MHz) and reads the echo return in each grid region. Differently sized transducers are available depending upon the area of the inspection region. For example, ultrasonic transducers having a diameter of 0.250" and 0.375" are available. Prior to beginning the inspection process, the surface of the copper bar 76 must be clean and free of any contaminants that can adversely affect the transmitted and received ultrasonic test signals.

If the copper bar 74 is not adequately brazed to the consolidation clip 70, an air pocket or void will be present between the mating surfaces. Since the void distorts the echo return, comparison of the actual return with a normal return from a properly mated surface allows void detection. Generally, a greater magnitude echo return indicates a void between the mating surfaces. The ultrasonic inspection process is based on a physical material property referred to as the acoustic impedance. Air has very high acoustic impedance and therefore incident ultrasonic energy is almost totally reflected (about 99.7% reflection) by air. A high quality brazed joint with no air voids between the mating surfaces produces a small echo return signal as most of the energy is absorbed by the brazed materials.

As ultrasonic energy is transmitted at each inspection site, the technician manually records the parameters of the echo return. After an entire overlap region 76 has been inspected, the number of problematic sites or the ratio of the problematic sites to the total number of sites is determined. In one inspection process, each inspection site is determined to either pass or fail the inspection based on the relationship between the return magnitude and a predetermined return threshold. The number of failed sites or the percent of failed sites to the total number of inspection sites is compared to a predetermined threshold, above which the brazed joint in that overlap region is considered unsatisfactory.

In one stator coil embodiment there are sixteen inspection sites in each overlap region 76. With four overlap regions on the top and bottom coils 18A and 18B, as illustrated in FIG. 5, there are 64 inspection sites for each coil end. Conventionally, a generator has 36 slots (see reference character 62 of FIG. 2) and thus 72 coils (a top and a bottom coil disposed in each slot), resulting in more than 1000 inspection sites. In addition to the large number of inspection sites, the prior art process is extremely tedious, as the inspector must manually reposition the ultrasonic transducer between the closely spaced inspection sites. One embodiment of the consolidation clip 70 has a width of about one inch, and is therefore segregated into three columns of 0.333-inch squares. Each square represents one inspection site. Another embodiment of a consolidation clip 70 has a width of about 1.25 inches, and is therefore segregated into three columns of 0.25 inch squares (i.e., there is one inspection site in each quarter-inch grid square). Thus it can be seen that manual positioning of the ultrasonic transducer in these small inspection sites requires the inspector to possess above average manual dexterity. The calculation for determining whether an inspection site has passed or failed is manually performed by the technician and thus subject to induced errors. There is no prior art process for automatically storing the return echo data.

BRIEF SUMMARY OF THE INVENTION

An ultrasonic inspection tool for determining the condition of a joint formed between a first and a second object. The securing component secures the tool relative to the joint. An arm of the tool is disposed proximate a surface of the first object and a motion imparting component scans the arm along the surface. An ultrasonic transducer/sensor supported by the arm transmits an ultrasonic signal to the joint and senses an ultrasonic echo from the joint. The signal is transmitted to and the echo is received from a plurality of joint zones. A processor responsive to the echo determines the condition of the joint.

BRIEF DESCRIPTION OF THE DRAWINGS

The foregoing and other features of the invention will be apparent from the following more particular description of the invention, as illustrated in the accompanying drawings, in which like reference characters refer to the same parts throughout the different figures. The drawings are not necessarily to scale, emphasis instead being placed upon illustrating the principles of the invention.

DETAILED DESCRIPTION OF THE INVENTION

Figure 1:
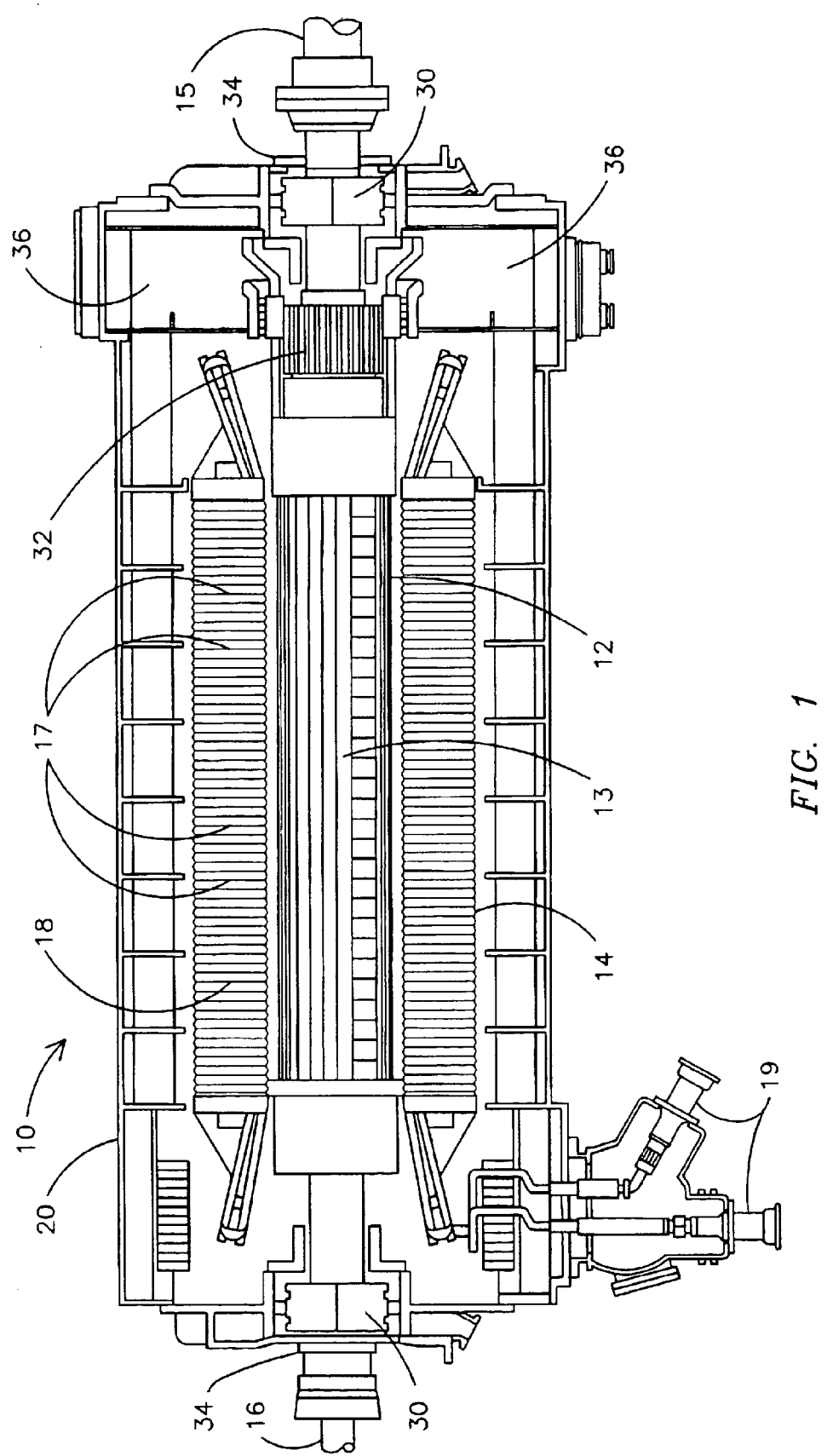
FIG. 1 is a cross-sectional view of an electric generator.
Figure 2:
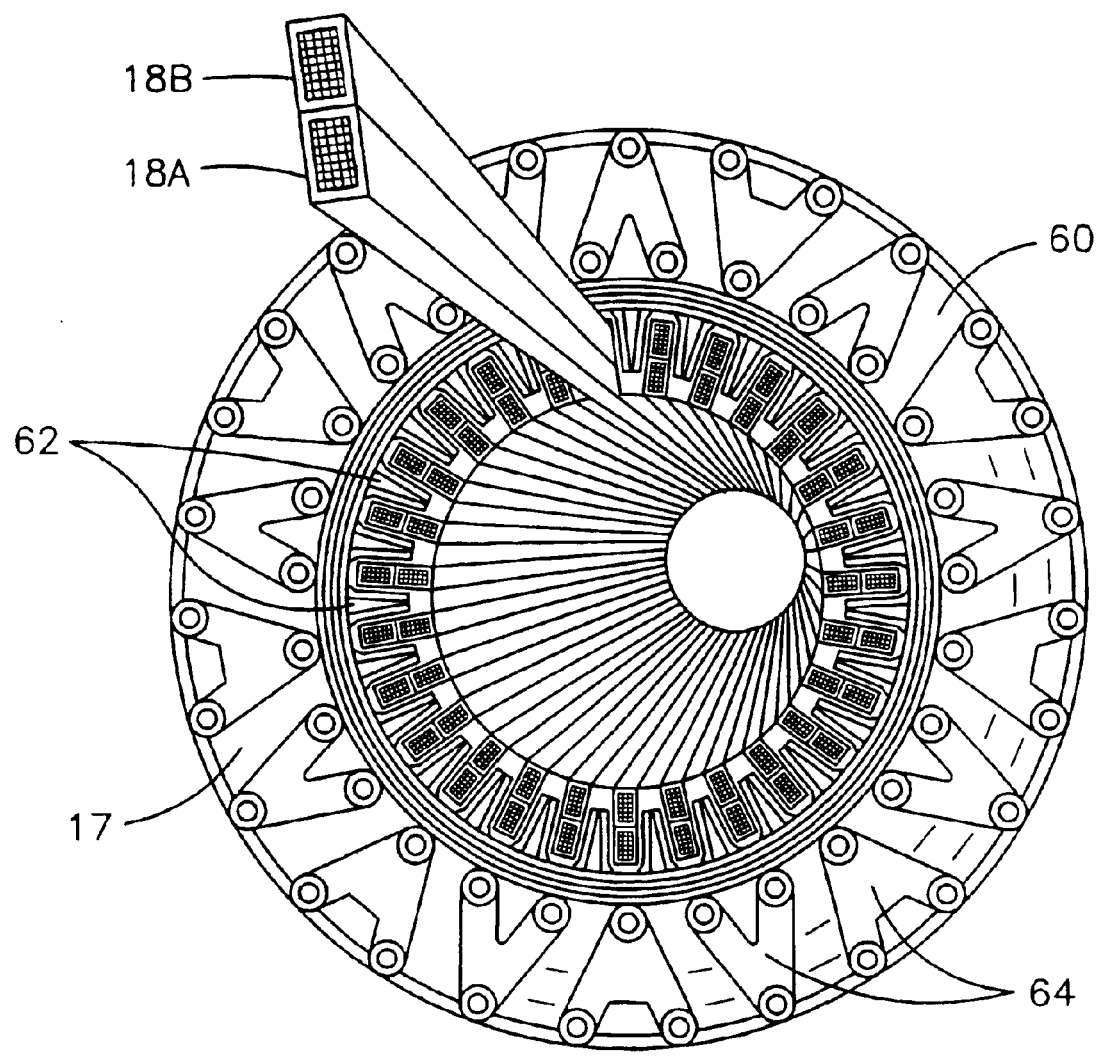
FIG. 2 is a cross-sectional view through the stator of FIG. 1.

Before describing in detail the automated ultrasonic inspection tool in accordance with the present invention, it should be observed that the present invention resides primarily in a novel and non-obvious combination of hardware elements and method steps. Accordingly, these elements and steps have been represented by conventional elements and steps in the drawings, showing only those specific details that are pertinent to the present invention so as not to obscure the disclosure with details that will be readily apparent to those skilled in the art having the benefit of the description herein.

The ultrasonic inspection tool 100 (see FIG. 6) of the present invention operates to inspect a joint formed between two joined objects. The joint can be formed, for example, by brazing or soldering the two objects. In other applications, the joint can be formed by an adhesive that bonds the two materials. One application of the present invention relates to inspection of the joint between the top and bottom coils 18A and 18B and the copper bar 74 as discussed above. Although the invention is described with respect to an inspection tool using ultrasonic energy to determine the joint condition, in other embodiments, other energy forms can be used to perform the inspection.

Figure 6:
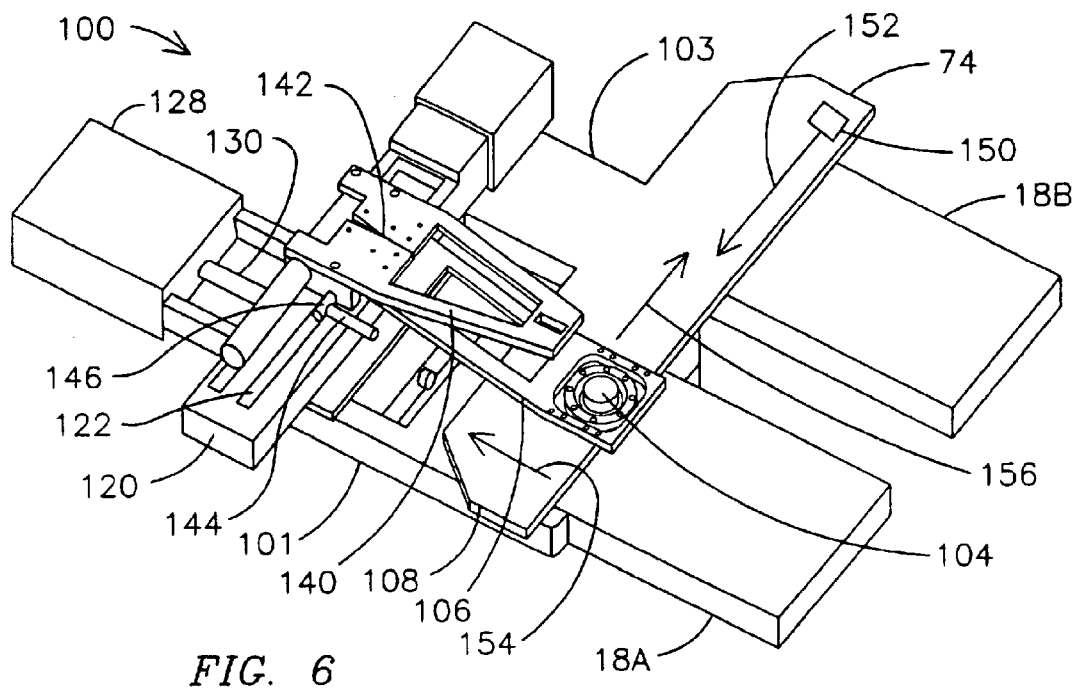
FIGS. 6 and 7 illustrate an inspection tool constructed according to the teachings of the present invention.
Figure 7:
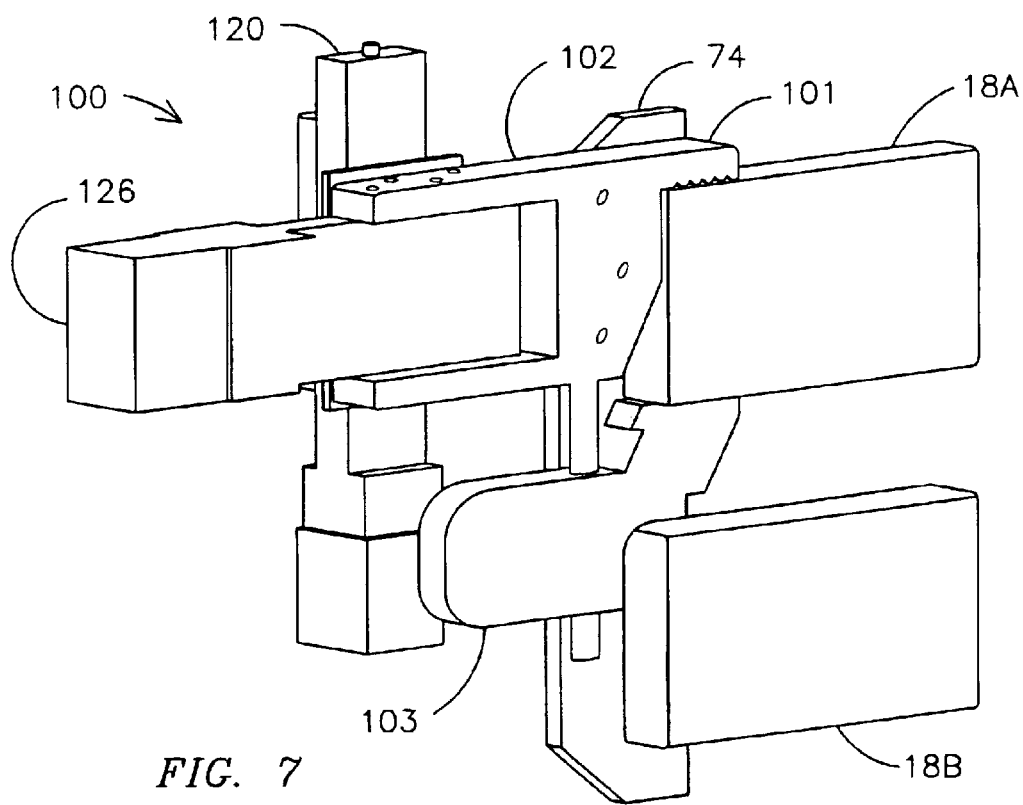

With reference to FIGS. 6 and 7, the tool 100 comprises a clamp 101 further comprising opposingly adjustable jaws 102 and 103, for attaching the tool 100 to the top coil 18A to inspect the joint between the top coil 18A and the copper bar 74. Thus the clamp 101 spans the width of the top coil 18A and is removably affixed thereto by locking the jaws 102 and 103 to capture the top coil 18A therebetween. Any of the known clamping and locking techniques can be employed to removably affix the clamp 101 to the coil 18A. Further, the clamp 101 and the jaws 102 and 103 can be modified to accommodate differently sized, shaped and spaced stator coils. Additionally, in another embodiment, the tool 100 is affixed to an external support structure such that there is no relative motion between the tool 100 and the joint to be inspected. As expected, motion between the tool 100 and the joint compromises the accuracy of the inspection results.

Figures 3A, 3B, 4, 5:
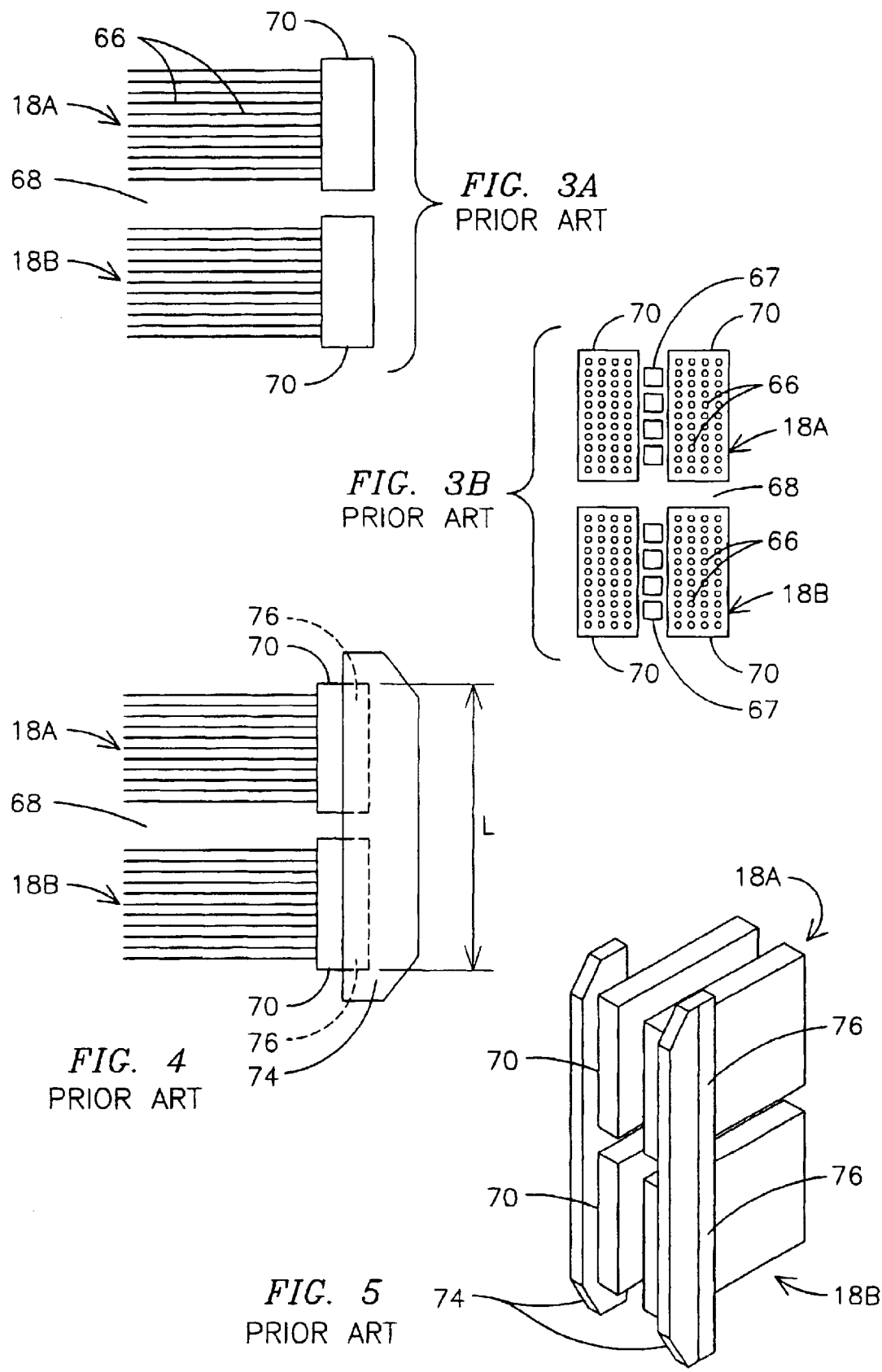
FIGS. 3A and 3B illustrate two views of an end region of a stator top and bottom coil of FIG. 2.
FIGS. 4 and 5 illustrate a copper bar interconnecting the top and bottom coils.

With reference to FIG. 6, an ultrasonic transducer/sensor 104 is carried by an arm 106 and disposed proximate a surface 108 of the copper bar 74. The inspection is conducted in a region bounded by the overlap region 76 between the copper bar 74 and the consolidation clip 70 affixed to the top coil 18A (see FIGS. 3A, 3B and 4) to determine the quality of the brazed or soldered joint between the copper bar 74 and the consolidation clip 70. During the inspection process the transducer/sensor 104 is controlled to move in both the longitudinal and transverse directions over the surface 108 to inspect the underlying joint at a grid-like plurality of inspection sites. In a preferred embodiment the transducer/sensor 104 operates using the known ultra-sonic pulse-echo technique, wherein the transducer/sensor 104 comprises both a transmitting element to emit the ultrasonic signal and a receiving element to sense the echo return. In one embodiment, the transducer/sensor 104 emits the ultrasonic signal substantially perpendicular to the joint.

As further shown in FIG. 6, the arm 106 is movably coupled to a slide unit 120. Longitudinal motion of the arm 106, and thus of the transducer/sensor 104, is imparted by a motor (e.g., a stepper or linear motor (not shown)) within the slide unit 120, for moving the arm 106 and the attached transducer/sensor 104 along a longitudinal track 122 of the slide unit 120.

The slide unit 120 is movably coupled to a slide unit 128, disposed perpendicular to the slide unit 120. A motor within the slide unit 128 imparts motion to the slide unit 128 along a transversal track 130, and thereby to the transducer/sensor 104 in the transversal direction. Thus, the combination of the slide units 120 and 128 moves the transducer/sensor 104 along two axes of the surface 108.

Each of the slide units 120 and 128 further comprises a position encoder (not shown), typically integrated with the motor, for providing a feedback signal representing the position of the transducer/sensor 104 on the surface 108. The position feedback information allows a processor, as further described below, to determine the position of the arm 106 and thus control the arm position, which in turn controls the position of the transducer/sensor 104. In one embodiment, each encoder comprises a rotary optical encoder mounted on the motor shaft. The shaft rotation information supplied by the encoder, coupled with knowledge of the pitch of a lead screw driven by the motor, allows calculation of the linear displacement of each slide unit 120 and 128. Using a known home or starting position and the linear displacement, the processor calculates the arm position. If not in the desired position, the arm position can be adjusted by the processor through control of the slide unit motors as will be discussed further below. In another embodiment, each slide unit 120 and 128 further comprises a limit switch for limiting travel of the arm 106 relative to the each slide unit 120 and 128.

Figure 8:
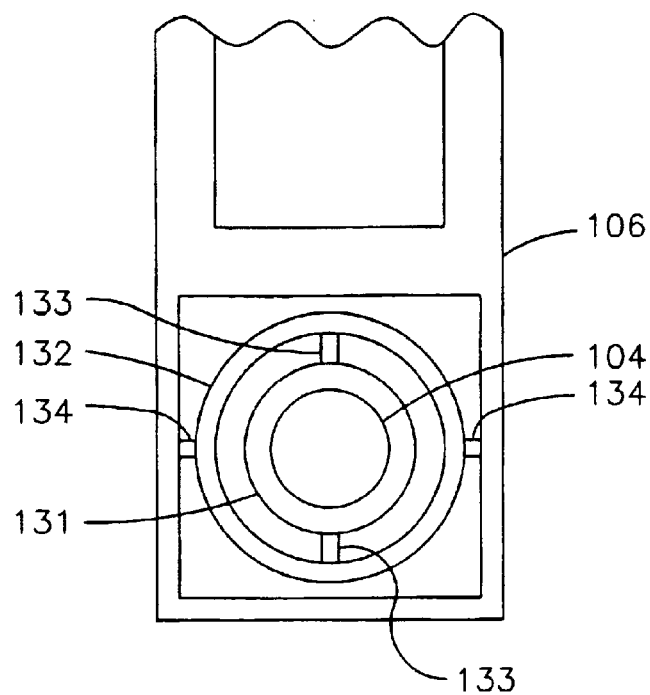
FIGS. 8, 9 and 10 illustrate an arm of the inspection tool of FIGS. 6 and 7.

As shown in FIG. 8, the transducer/sensor 104 is mounted to the arm 106 via rings 131 and 132 to allow rotation about universal joints 133 and 134. This mounting configuration allows the transducer/sensor 104 to rotate about two axes (i.e., two degrees of freedom) to conform to any irregularities that might be present on the surface 108 or on the surface of the couplant applied to the surface 108, as the arm 106 translates over the surface 108.

A spring or other biasing component disposed between the arm 106 and a cover plate 140 (see FIG. 6) in a region indicated approximately by reference character 142 supplies a downwardly directed force to ensure the transducer/sensor 104 maintains contact with the couplant.

Manual rotation of a lever 144 (see FIG. 6) mounted on a shaft 146 operates a cam (not shown) also mounted on the shaft 146 and positioned below the arm 106, to lift and lock the arm 106 into a position away from the surface 108. With the arm in this raised position the tool 100 can be moved to another coil for inspection. After securing the tool 100, the arm 106 is returned to the inspection position by manual rotation of the lever 144.

After applying couplant, typically a gel-based material, to the surface 108, the inspection process according to an embodiment of the present invention begins by clamping for inspection of another surface, the inspection tool 100 onto a stator coil, such as the top coil 18A. See FIGS. 6 and 7. The arm 106 will have been previously moved to the raised position through action of the lever 144, and is now lowered to the surface of the couplant, again by manual action of the lever 144. The couplant is advantageous to reduce air gaps between a bottom surface of the transducer/sensor 104 and the surface 108, where the air gaps can attenuate the transmitted and echo ultrasonic signals.

The transducer/sensor 104 is moved to a home position by the slide units 120 and 128 as described above. One exemplary home position at a corner of the copper bar 74 is a region 150. By energizing the motor within the slide unit 120, the transducer/sensor 104 moves in a longitudinal direction along an axis 152, stopping at quarter-inch intervals, for example, to conduct an ultrasonic inspection. For example, to conduct an ultrasonic inspection, i.e., transmitting an ultrasonic signal and sensing the echo return. After conducting a series of inspections at a plurality of inspection sites along the axis 152, the transducer/sensor 104 is displaced along a transverse axis 154, by energizing the motor within the slide unit 128. The transducer/sensor 104 then translates along an axis 156, under control of the motor within the slide unit 120, to conduct another series of ultrasonic inspections. By undergoing a series of such longitudinal and transversal translations, the transducer/sensor 104 covers substantially all of the surface 108, which represents the region of overlap between the copper bar 74 and the consolidation clip 70.

As discussed above in conjunction with the FIG. 5 embodiment of a stator coil, there are four overlap regions 74. Each overlap region 74 is inspected using the tool 100 according to the teachings of the present invention. After inspecting one overlap region 74, for example the right side of the top coil 18A, the arm 106 is moved to a raised position by manual action of the lever 144. The tool 100 is unclamped and clamped onto the right side of the bottom coil 18B. The arm 106 is lowered by action of the lever 144, and the inspection proceeds as described above. Upon completion of the second inspection, the tool 100 is relocated to the left side of the top and bottom coils 18A and 18B for inspecting the overlap regions associated therewith.

In another embodiment of the tool 100, the arm 106 is controllably raised away from the surface of the couplant after inspecting a site, moved to the next inspection site, and controllably lowed to the couplant surface. Thus in this embodiment the arm 106 and the attached transducer/sensor 104 do not drag through the couplant material as the arm translates between inspection sites, avoiding a resultant build-up of couplant on the transducer/sensor 104 that can adversely affect the test results.

Figure 9:
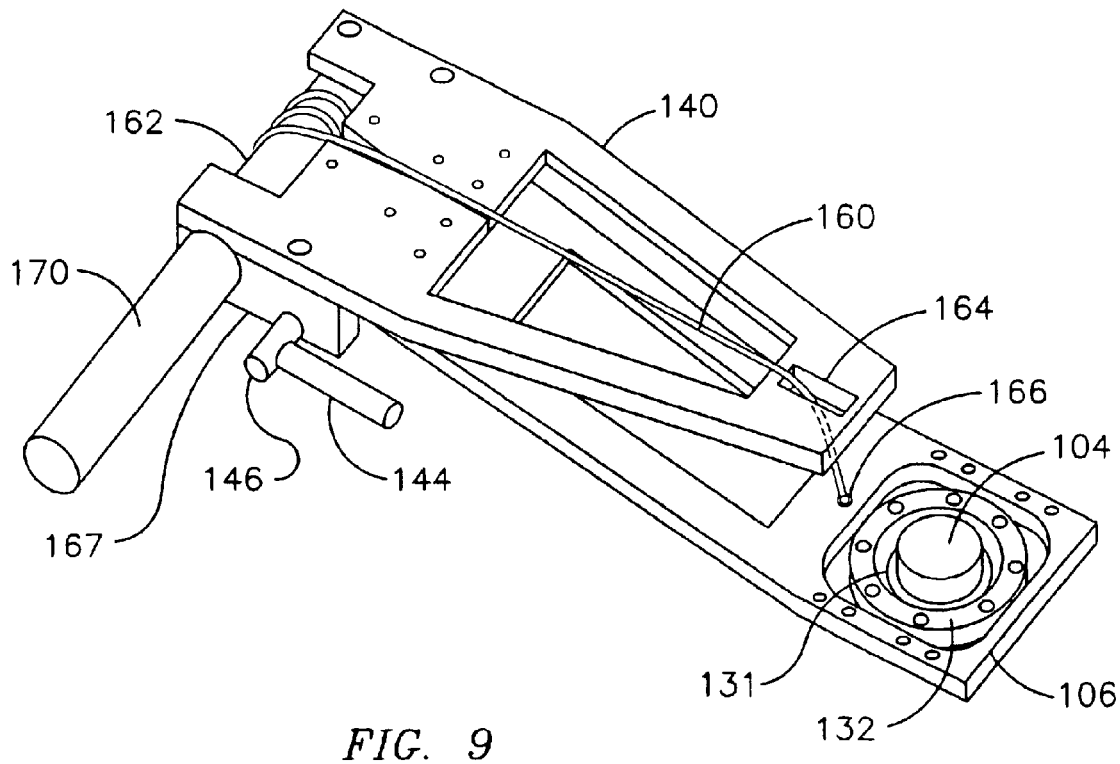

FIG. 9 illustrates the components associated with this embodiment for imparting arm motion along a third axis. A cable 160 extends from a drum 162 along the cover plate 140 to a pulley 164 mounted on a bottom-facing surface at a forward end of the cover plate 140 as shown. The cable 160 is affixed to an attachment point 166 on the arm 106. The drum 162 is rotatably supported by a frame 167. A motor 170 in rotational cooperation with the drum 162 operates to wind or unwind the cable 160 from the drum, thereby raising or lowering the arm 106 relative to the surface 108. In raising the arm 106, the force exerted by the motor 170 overcomes the bias force exerted by the spring on the arm 106 as previously discussed. In lowering the arm 106, the spring bias force drives the arm 106 in the direction of the surface 108. The motor 170 further comprises a position encoder (not shown) from which the position of the arm 106 relative to the surface 108 can be determined.

Figure 10:
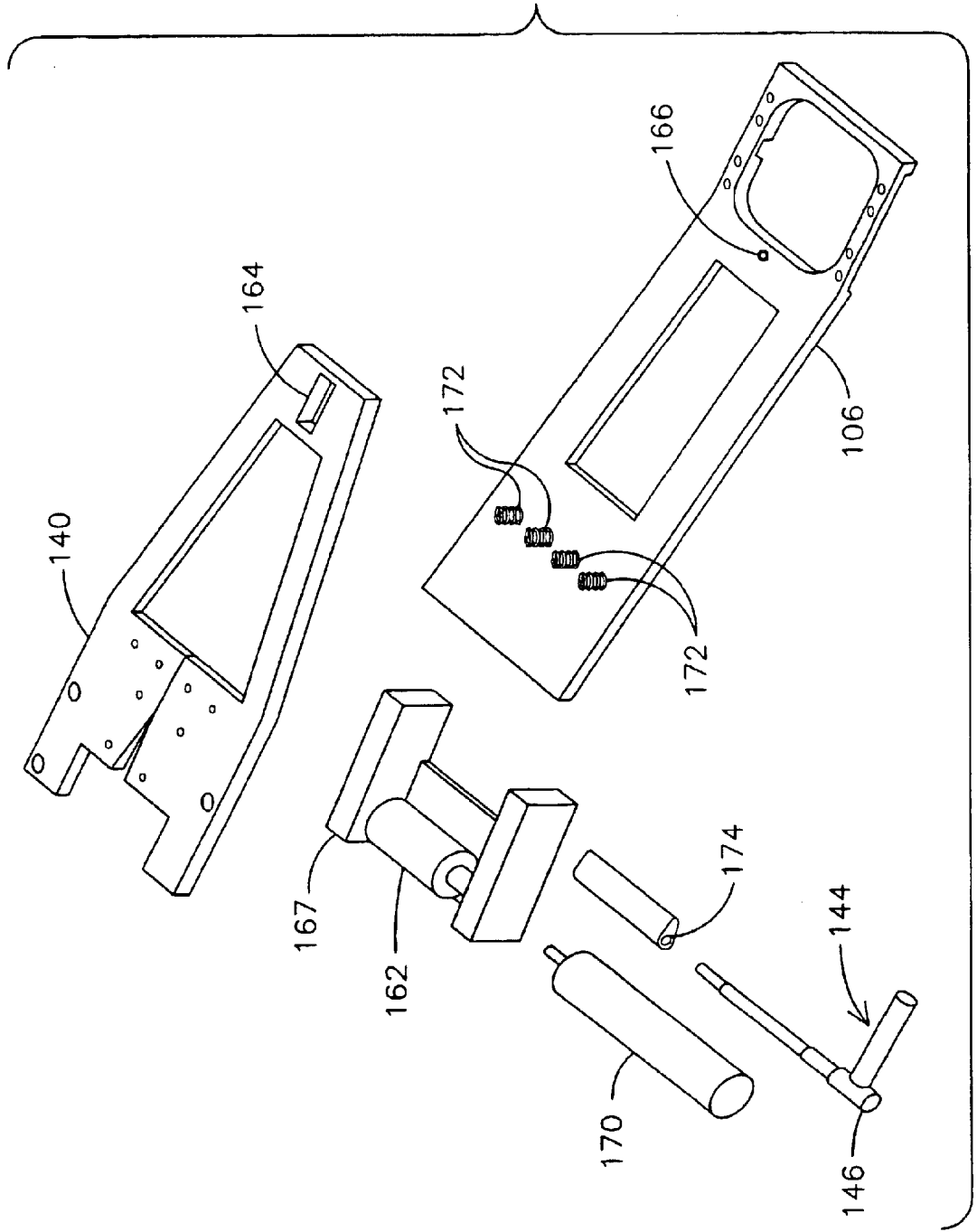

FIG. 10 is an exploded view of the components of FIG. 9, further illustrating springs 172 (in this embodiment four such springs 172) for supplying the aforementioned bias force. Also illustrated is the previously described cam 174 controllably operated by the lever 144 for lifting and locking the arm 106 in a raised position.

Figure 11:
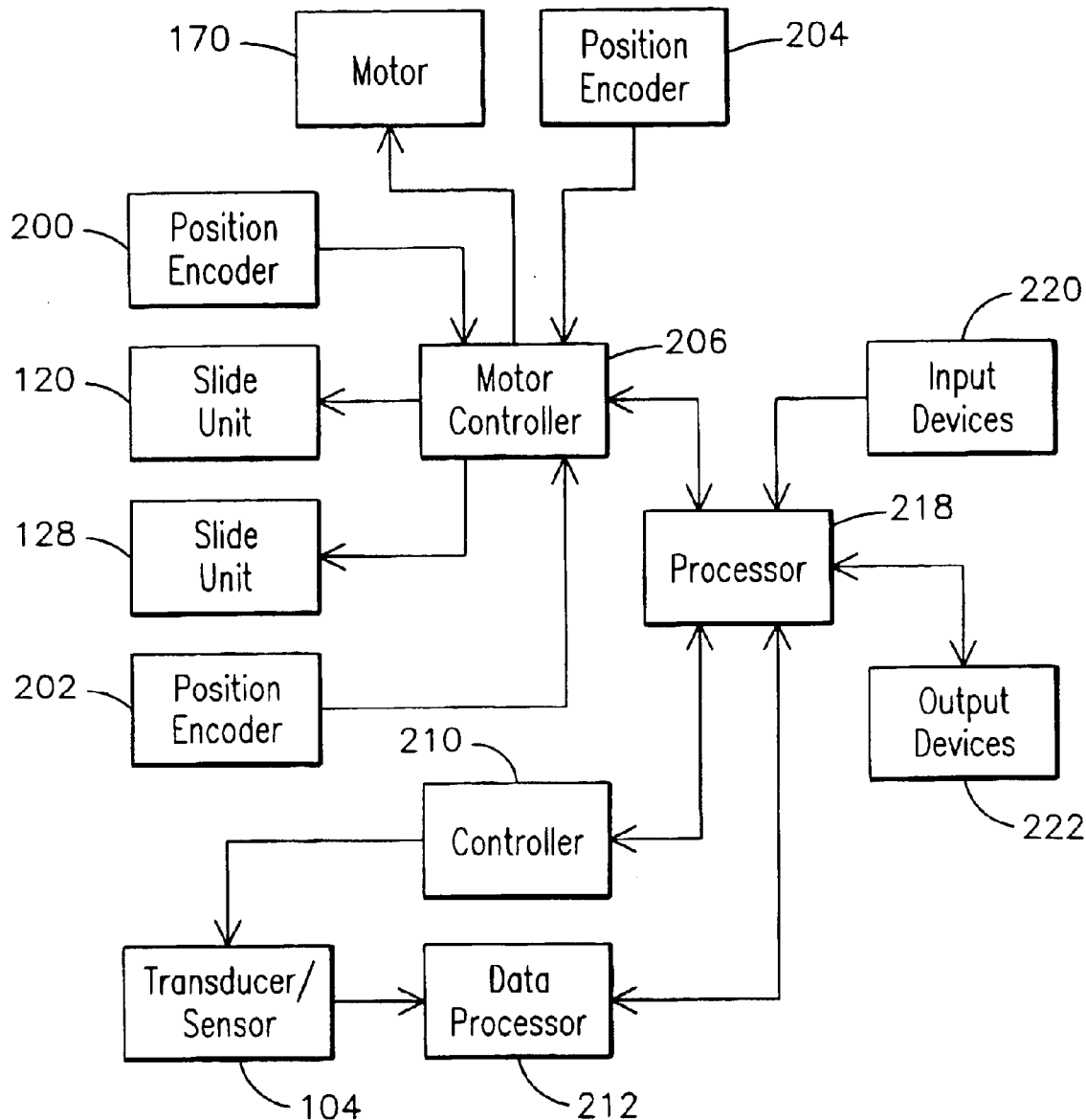
FIG. 11 is a block diagram depicting the functional elements of the inspection tool of the present invention.

FIG. 11 illustrates certain control and data processing components associated with the tool 100. In response to position information supplied by position encoders 200 and 202 within the side units 120 and 128, and a position encoder 204 associated with the motor 170, a motor controller 206 controls the motor within each of the slide units 120 and 128, and the motor 170 to move the arm 106. With the availability of position feedback information, position control of the transducer/sensor 104 is improved over the prior art, resulting in more accurate placement of the transducer/sensor 104 on the surface 108 and improved inspection results.

The transducer/sensor 104 is responsive to a controller 210 for producing the ultrasonic signal. A software or firmware driven data processor 212 is responsive to the transducer/sensor 104 for receiving an electrical signal generated by the transducer/sensor 104 in response to the ultrasonic echo. The data processor 212 collects, processes and interprets the echo signal.

A software or firmware-driven processor 218 exercises control over and receives input signals from the motor controller 206, the controller 210 and the data processor 212 for controlling the overall inspection process. User-operable input devices 220 supply user-defined inspection parameters to the processor 218 for controlling the inspection. For example, the user enters the size of the joint to be tested through one of the input devices 220. Once the tool is connected to the joint as described above, the user initiates the inspection process by activating one of the input devices 220. In response, under software control the transducer/sensor 104 is moved to the home position and the inspection proceeds without further intervention. The echo return signals are read and analyzed as described below. However, at any time during the inspection process, the user can interrupt the process and conduct a manual or hand-scan inspection, activating the appropriate manual input device to transmit of the ultra-sonic signal at each inspection site. In this operational mode, the tool 100 reads and analyzes the echo returns.

Various output devices, also responsive to the processor 218 and indicated by reference character 222, provide for the display, printout, or storage of the inspection results. In particular, the tool 100 provides a braze joint inspection report including the echo return values and an indication of the joint quality based on the echo return values.

Raw data representative of the echo return is stored in digital file form in a memory associated with either the data processor 212 or the processor 218. To analyze the data, either the data processor 212 or the processor 218 retrieves the echo information file from memory and analyzes the echo to determine the quality of the brazed joint at the inspection point. As is known to those skilled in the art, several analysis procedures can be carried out on the echo data. The simplest process analyzes the echo returns from each grid zone of the surface 108 and characterizes each as indicating a pass or failed grid zone. The percentage of zones that have passed the test is then compared with the total number of inspection test sites. If the result is greater than a predetermined threshold (for example 65%), then the joint between the copper bar 74 and the consolidation clip 70 is deemed satisfactory, as the likelihood of a joint failure is considered to be minimal. If the number of acceptable inspection sites is less than this predetermined value, then the test is re-executed and/or the joint is re-brazed.

An inspection performed using the inspection tool of the present invention, provides a faster and more efficient inspection process than disclosed by the prior art, thus reducing outage time for an operating generator and improving inspection results. The process of automatically reading the reflected return and calculating the quality of the joint reduces the likelihood of error and provides permanent data storage for the inspection results.

While the invention has been described with reference to preferred embodiments, it will be understood by those skilled in the art that various changes may be made and equivalent elements may be substituted for elements thereof without departing from the scope of the present invention. For example the inspection tool can be adapted to inspect joints wherein the components have been bonded by other processes, including a soldering or welding process. The scope of the present invention further includes any combinations of the elements from the various embodiments set forth herein. In addition, modifications may be made to adapt the teachings of the present invention to a particular situation without departing from its scope. Therefore, it is intended that the invention not be limited to the particular embodiment disclosed as the best mode contemplated for carrying out this invention, but that the invention will include all embodiments falling within the scope of the appended claims.

What is claimed is:

1. An inspection tool for determining the condition of a joint formed between a first and a second object, wherein the first object comprises a generator stator winding and the second object comprises a copper bar, the inspection tool comprising:

an arm disposed proximate a surface of the first object, wherein the surface overlies the joint;

a motion-imparting component for scanning the arm along the surface;

a sensor supported by the arm for inspecting the joint, wherein the joint is subdivided into a plurality of zones, and wherein an inspection signal is generated by the sensor for each of the plurality of zones; and a processor responsive to the inspection signal from the plurality of zones for determining a condition of the joint.

2. The inspection tool of claim 1 further comprising a securing component for removably attaching the tool proximate the joint.

3. The inspection tool of claim 2 wherein the securing component further comprises a clamp for removably attaching the tool to one of the first or the second objects.

4. The inspection tool of claim 1 wherein the plurality of zones comprises a plurality of substantially equally sized grid regions.

5. The inspection tool of claim 1 wherein the joint formed between the first and the second objects is selected from between a brazed joint and a soldered joint.

6. The inspection tool of claim 1 wherein the processor stores information relative to the inspection signal from the plurality of zones.

7. The inspection tool of claim 1 wherein the inspection signal comprises an ultrasonic signal.

8. The inspection tool of claim 1 further comprising a transducer supported by the arm for transmitting an incident signal toward the joint, and wherein the inspection signal comprises a reflection of the incident signal from the joint.

9. An ultrasonic inspection tool for determining the condition of a joint formed between a first and a second object, wherein the first object comprises a generator stator winding and the second object comprises a copper bar, the ultrasonic inspection tool comprising:

a securing component for removably attaching the tool proximate the joint;

an arm disposed proximate a surface of the first object, wherein the surface overlies the joint;

a motion-imparting component for scanning the arm along the surface;

an ultrasonic transducer/sensor supported by the arm for transmitting an ultrasonic signal toward the joint and for sensing an ultrasonic echo, wherein the joint is subdivided into a plurality of zones, and wherein the signal is transmitted within and the echo is received from one or more of the plurality of zones; and a processor responsive to the echo from the plurality of zones for determining the condition of the joint.

10. An inspection tool for a generator stator winding, wherein the winding comprises a top and a bottom coil interconnected by a copper bar forming a first joint between the top winding and the copper bar and a second joint between the bottom winding and the copper bar, the ultrasonic inspection tool comprising:

a securing component for removably attaching the tool to the top or the bottom winding;

an arm disposed proximate a surface of the copper bar, wherein the surface comprises a region of the copper bar substantially bounded by the underlying first or the second joint;

a motion-imparting component for scanning the arm along the surface;

an sensor supported by the arm, wherein an inspection signal is generated by the sensor for a plurality of joint zones; and a processor responsive to the inspection signal for the plurality of joint zones for determining the condition of the first or the second joint.

* * * * *